United States Patent
Ehrismann et al.

(10) Patent No.: US 7,790,323 B2
(45) Date of Patent: Sep. 7, 2010

(54) POLYMER ELECTROLYTE, HALF-CELL FOR ELECTROCHEMICAL MEASUREMENTS, AS WELL AS THE USE THEREOF

(75) Inventors: Philippe Ehrismann, Uster (CH); Wolfgang Haller, Chevy Chase, MD (US)

(73) Assignee: Mettler-Toledo AG, Greifensee (CH)

( * ) Notice: Subject to any disclaimer, the term of this patent is extended or adjusted under 35 U.S.C. 154(b) by 577 days.

(21) Appl. No.: 11/494,452

(22) Filed: Jul. 28, 2006

(65) Prior Publication Data
US 2007/0020527 A1  Jan. 25, 2007

Related U.S. Application Data

(63) Continuation of application No. PCT/EP2005/050293, filed on Jan. 24, 2005.

(30) Foreign Application Priority Data
Jan. 28, 2004  (EP)  ................... 04100299

(51) Int. Cl.
H01M 10/40 (2006.01)
C25B 13/00 (2006.01)
G01N 27/26 (2006.01)

(52) U.S. Cl. .................. 429/314; 429/317; 204/296; 204/421

(58) Field of Classification Search .................. None
See application file for complete search history.

(56) References Cited

U.S. PATENT DOCUMENTS

| 5,360,529 A | * | 11/1994 | Edwards et al. | ............. | 204/435 |
| 5,549,988 A | * | 8/1996 | Reichert et al. | ............. | 429/317 |
| 6,468,408 B2 | * | 10/2002 | Thrier et al. | ................ | 204/435 |
| 2003/0183517 A1 | * | 10/2003 | Ehrismann et al. | .......... | 204/296 |

FOREIGN PATENT DOCUMENTS

| EP | 0 615 525 B1 | | 5/1998 |
| EP | 0 859 420 A2 | | 8/1998 |
| EP | 1 124 132 A1 | | 8/2001 |
| WO | WO 93/11174 | * | 6/1993 |
| WO | WO 97/35350 | | 9/1997 |

* cited by examiner

Primary Examiner—Dah-Wei Yuan
Assistant Examiner—Angela Martin
(74) Attorney, Agent, or Firm—Buchanan Ingersoll & Rooney PC

(57) ABSTRACT

A polymer electrolyte for an electrochemical half-cell, such as a reference half-cell, contains a polymer which can be produced by polymerization of N-acryloyl-amino-ethoxy-ethanol or by co-polymerization of N-acryloyl-amino-ethoxy-ethanol with at least one further monomer component.

18 Claims, 1 Drawing Sheet

US 7,790,323 B2

POLYMER ELECTROLYTE, HALF-CELL FOR ELECTROCHEMICAL MEASUREMENTS, AS WELL AS THE USE THEREOF

RELATED APPLICATIONS

This application claims priorities under 35 U.S.C. §119 to EP Application No. 04100299.9 filed Jan. 28, 2004, and as a Continuation Application under 35 U.S.C. §120 to PCT Application No. PCT/EP2005/050293 filed as an International Application on Jan. 24, 2005 designating the U.S., the entire contents of which are hereby incorporated by reference in their entireties.

BACKGROUND

1. Technical Field

A polymer electrolyte for an electrochemical half-cell, a half-cell as well as uses of a half-cell and a polymer electrolyte are disclosed.

2. Background Information

Numerous types of half-cells for electrochemical measurements are known, e.g., for potentiometric or amperometric measurements. Such half-cells can be configured in particular as reference electrodes that are used in combination with potentiometric or amperometric sensors. Such reference electrodes provide a reference potential as as constant possible.

In one kind of reference electrode, a liquid reference electrolyte is contained inside a housing, for example an aqueous solution of potassium chloride which can be brought into contact with a liquid measurement medium by way of a liquid connection (also referred to as "liquid junction"). In order to avoid or reduce the occurrence of an undesirable exchange of substance between the measurement medium and the reference electrolyte, the liquid connection can be configured as a more or less porous diaphragm. However, liquid connections of this kind have pores that can become contaminated or even obstructed, which can lead to errors in the electrical potential and possibly to interruptions.

A further type of reference electrode has a single opening or a plurality of openings instead of a diaphragm, whereby the aforementioned contamination can largely be avoided. However, in order to prevent the reference electrolyte from draining out, this configuration uses a reference electrolyte that is not capable of liquid flow instead of using the liquids or gels that form the reference electrolyte. Particularly suitable for this purpose is a polymer electrolyte that is present in the form of a hydrogel containing for example a saturated aqueous solution of potassium chloride, such as with additional potassium chloride in suspended form.

A reference electrode is described in EP 1 124 132 A1, the disclosure of which is hereby incorporated by reference in its entirety. A polymer electrolyte contains a polymer based on monomers selected from N-substituted acrylamides and/or methacrylates. The N-substituted acrylamides are selected for example from N,N-dimethyl-acrylamide, N-(tris(hydroxyl-methyl)-N-methyl-acrylamide, N-hydroxyl-methyl-acrylamide, N-hydroxyl-ethyl-acrylamide, N-glycerin-acrylamide and combinations thereof. The monomers used in this electrode are used to make polymer electrolytes that have an unsatisfactory level of stability against acids and bases, a poor stability against hydrolysis, as well as a low polarity.

SUMMARY

Polymer electrolytes are disclosed that are particularly suitable for electrochemical half-cells, in particular for reference half-cells. In comparison to the known electrolytes, the electrolytes disclosed herein can have a higher polarity as well as an improved stability against hydrolysis. A half-cell, as well as to name uses for the half-cell and the polymer electrolytes are also disclosed.

BRIEF DESCRIPTION OF THE DRAWINGS

The one FIGURE of the drawing schematically illustrates an exemplary reference electrode for electrochemical measurements in a lengthwise sectional view.

DETAILED DESCRIPTION

Figure 1:
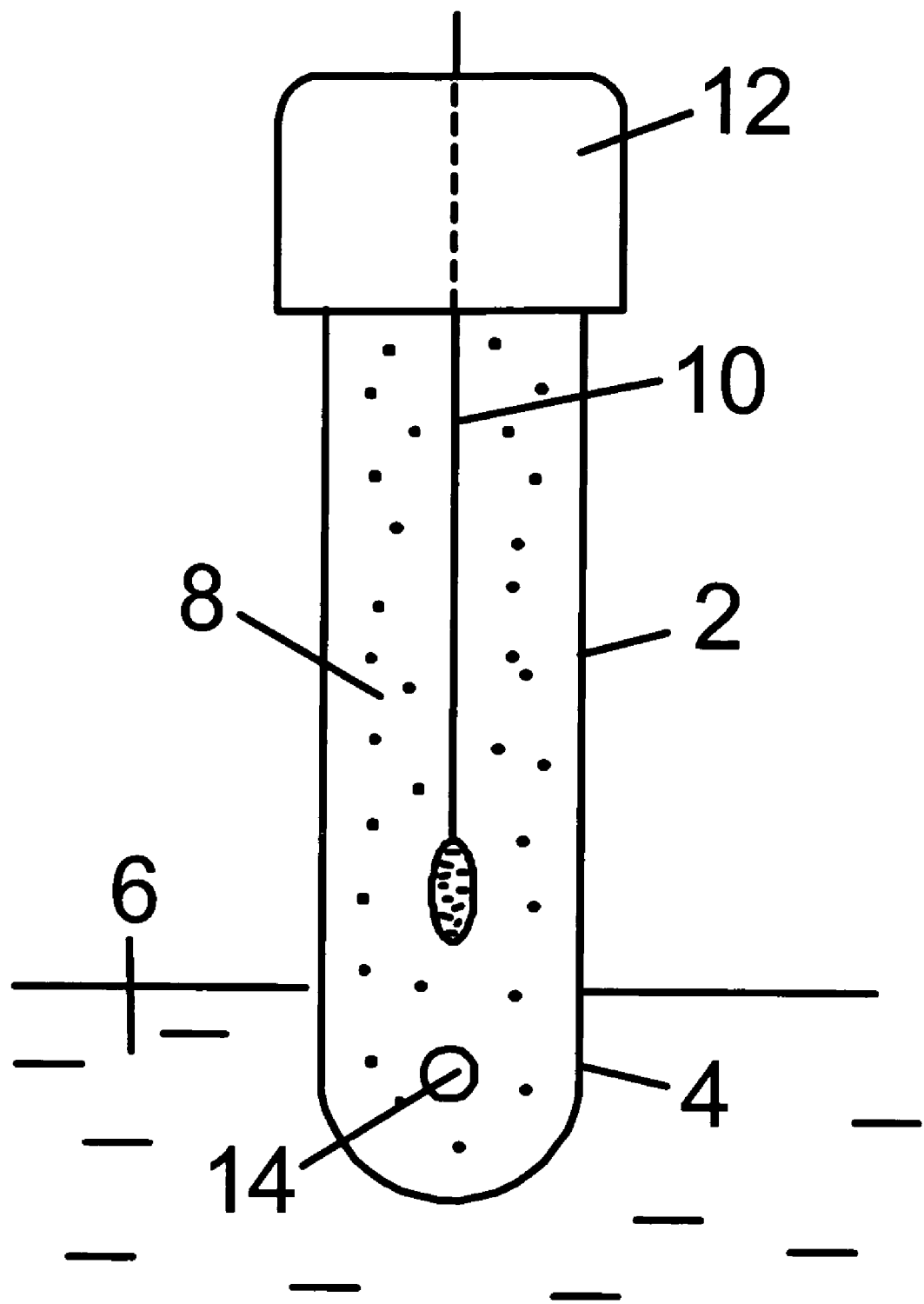

Exemplary polymer electrolytes disclosed herein contain a polymer that can be formed of and produced by polymerization of N-acryloyl-amino-ethoxy-ethanol or by co-polymerization of N-acryloyl-amino-ethoxy-ethanol with at least one further monomer component. The polymer electrolytes are distinguished by, for example, a good level of resistance and stability against acids as well as against bases. In addition, the polymer electrolytes can have a good level of stability in water as well as in organic solvents.

The half-cell disclosed herein, which can be used as a component in potentiometric or amperometric sensors, contains one of the polymer electrolytes described herein. The polymer electrolyte can be used as solid-phase electrolyte in a battery half-cell.

The polymer can contain a hydroxyl-alkyl-methacrylate, with the latter being preferably a 2-hydroxyl-ethyl-methacrylate and/or 3-hydroxyl-propyl-methacrylate. With this further monomer component, the polarity of the polymer electrolyte can be influenced in an advantageous manner, where the polarity can be adjusted over a wide range through the choice of the ratio between the respective quantities of the further monomer component and the first monomer component.

Exemplary embodiments are advantageous in connection with a half-cell with a glass housing. With the polymer containing a silylized alkyl-methacrylate as the further monomer component, preferably 3-(tri-methoxy-silyl)-propyl-methacrylate, one achieves a degree of adhesion of the polymer electrolyte to the glass housing, whereby a longer life of the half-cell and in particular a better pressure resistance and wash-out resistance are obtained.

Alternative embodiments can additionally contain a concentrated aqueous solution of a salt or salt mixture, which is advisable for the use in polar measurement media. An exemplary polymer electrolyte contains a mixture of an organic solvent and a concentrated aqueous solution of a salt, which makes this electrolyte suitable for use primarily in measurement media with a low degree of polarity. The organic solvent can be selected from the group consisting of glycerin, ethylene glycol, methanol, ethanol, n-propanol, isopropanol, acetone as well as mixtures thereof. It can be particularly advantageous if an additional amount of salt is present in suspended form. With the increased salt content, one can achieve a longer working life of the half-cell before the salt is washed out due to contact with the measurement medium. On the other hand, the advancing salt deficiency due to wash-out can be determined directly by visual observation of the wash-out and deficiency front that forms itself as a border between an area of the polymer electrolyte that is turbid due to the salt suspension and an area that is comparatively clearer due to the absence of the salt suspension. The salt referred to in this context can be selected from the group that consists for example of potassium chloride, sodium chloride, lithium chloride, potassium nitrate, potassium perchlorate, sodium formiate, lithium acetate, lithium sulfate, ammonium chloride, methyl-ammonium chloride, dimethyl ammonium chloride, trimethyl ammonium chloride as well as mixtures thereof. However, the salt can also be, e.g., a further ionic organic halogenide. Furthermore, the salt can form a redox system.

The half-cell disclosed herein can comprise an open liquid connection between the polymer electrolyte and a surrounding medium—normally a measurement medium or a liquid sample. This configuration is possible because, for example, the polymer electrolyte is present substantially in solid form and thus cannot escape via the open liquid connection. By omitting a diaphragm, undesirable potentials of interference in the area of the liquid connection can largely be avoided.

The reference electrode shown in the drawing FIGURE has a tubular housing 2 made of glass or a polymer material, whose lower end 4 is immersed in a measurement medium 6 in the illustrated example. The interior space of the housing 2 is filled with a polymer electrolyte 8 in which a conductor element 10 is immersed. The conductor element 10 is formed for example of a chlorinated silver wire which is routed to the outside by way of an upper enclosure part 12 of the housing 2. An opening 14 near the lower end 4 serves as liquid connection between the polymer electrolyte 8 and the measurement medium 6.

The polymer electrolyte 8 is formed advantageously inside the housing 2 by first bringing the required reactants, in particular the appropriate monomer components, into the interior space and by subsequently performing the polymerization. In the latter reaction a solidification takes place, so that the resultant polymer electrolyte 8 cannot escape from the opening 14.

Further embodiments are possible besides the reference electrode shown in the drawing FIGURE. The reference electrode can in particular be combined in a way that is known per se with a measuring electrode, for example a pH electrode, to form a single rod measuring chain. But other types of electrochemical half-cells, too, can be equipped with the polymer electrolyte, e.g., for amperometric measurements. The polymer electrolyte can further be used as solid-phase electrolyte in a battery half-cell.

The method for producing N-acryloyl-amino-ethoxy-ethanol, also known as N-(2-hydroxy ethoxy)-ethyl-acrylamide, is described, e.g., in EP 0615 525 B1, the disclosure of which is hereby incorporated by reference in its entirety.

PRACTICAL EXAMPLES

The polymer reference systems produced in accordance with the following examples exhibit very stable potentials in comparison to known liquid Ag/AgCl reference half-cells. The only slight differences between potentials are to be attributed to minor differences in the activity of the chloride ions. Due to these advantageous properties, the systems described here are very well suited for example as reference half-cells in potentiometric measuring chains.

To produce polymer electrolytes in accordance with exemplary embodiments, monomer solutions were assembled with a composition according to the following table and homogenized under cooling at 15 to 20° C. The mixtures obtained in this manner were filled into electrodes having a tubular glass housing. Through a subsequent heat treatment of the filled electrode, a polymerization was induced which led to the formation of the polymer electrolytes.

The electrochemical voltages measured against conventional sleeve junction references were in all cases smaller than 4 mV, which in principle indicates a good suitability. Further properties of the polymer electrolytes are summarized hereinafter.

TABLE

Composition (percentages by weight*)

| Component | Expl. 1 | Expl. 2 | Expl. 3 | Expl. 4 |
|---|---|---|---|---|
| N-acryloyl-amino-ethoxy ethanol | 10% | 11% | 9% | 8% |
| hydroxyl-ethyl-methacrylate | 0% | 0% | 2% | 2% |
| hydroxyl-propyl-methacrylate | 0% | 0% | 0% | 1% |
| KCl | 10% | 11% | 9% | 9% |
| Glycerin | 32% | 33% | 29% | 29% |
| silicic acid | 7% | 0% | 12% | 12% |
| Water | 40% | 44% | 37% | 37% |
| 3-(trimethoxy-silyl)-propyl-methacrylate | 0.2% | 0.0% | 0.0% | 0.0% |
| methylene-bis-acrylamide (MBA) | 0.0% | 0.2% | 0.2% | 0.2% |
| initiator (ammonium persulfate) | 0.0% | 0.0% | 0.4% | 0.4% |

*Due to rounding of the weight percentages, their sums add up to less than 100%

The polymer electrolyte according to example 1 is a turbid gel of high solidity with a tendency to expand in water.

The polymer electrolyte according to example 2 is a clear gel which in comparison to example 1 is more brittle and likewise has a tendency to swell up in water.

The polymer electrolyte according to example 3 is a turbid gel of high solidity which in comparison to examples 1 and 2 has a smaller polarity and thus has less of a tendency to swell up in water.

The polymer electrolyte according to example 4 likewise has a lower polarity.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE SYMBOLS

2 housing
4 lower end of 2
6 measurement medium
8 polymer electrolyte
10 conductor element
12 upper enclosure part of 2
14 opening of 2

The invention claimed is:

1. Half-cell for electrochemical measurements, comprising a polymer electrolyte comprising a polymer formed of N-acryloyl amino ethoxy ethanol or of N-acryloyl amino ethoxy ethanol co-polymerized with at least one further monomer component.

2. Half-cell according to claim 1, wherein an open liquid connection is provided between the polymer electrolyte and a surrounding medium.

3. Half-cell according to claim 1 in combination with a potentiometric or amperometric sensor.

4. Half-cell according to claim 1, wherein the polymer comprises a hydroxyl-alkyl-methacrylate as the further monomer component.

5. Half-cell according to claim 1, wherein the polymer comprises a silylized alkyl-methacrylate as the further monomer component.

6. Half-cell according to claim 1, wherein the polymer electrolyte additionally comprises a concentrated aqueous solution of a salt or of a salt mixture.

7. Half-cell according to claim 1, wherein the polymer electrolyte additionally comprises a mixture of an organic solvent and an aqueous solution of a salt.

8. Half-cell according to claim 7, wherein the organic solvent is selected from the group consisting of glycerin, ethylene glycol, methanol, ethanol, n-propanol, isopropanol, acetone and mixtures thereof.

9. Half-cell according to claim 6, wherein the salt is present in suspended form.

10. Half-cell according to claim 6, wherein the salt is selected from the group consisting of potassium chloride, sodium chloride, lithium chloride, potassium nitrate, potassium perchlorate, sodium formiate, lithium acetate, lithium sulfate, ammonium chloride, methyl-ammonium chloride, dimethyl-ammonium chloride, trimethyl-ammonium chloride and mixtures thereof.

11. Half-cell according to claim 1, wherein the polymer electrolyte is a solid-phase electrolyte.

12. Half-cell according to claim 1, wherein the half-cell is a reference half-cell.

13. Half-cell according to claim 4, wherein the polymer comprises, as the further monomer component, 2-hydroxyl-ethyl-methacrylate and/or 3-hydroxyl-propyl-methacrylate.

14. Half-cell according to claim 5, wherein the polymer comprises a 3-(tri-methoxy-silyl)-propyl-methacrylate as the further monomer component.

15. Half-cell according to claim 4, wherein the polymer electrolyte additionally comprises concentrated aqueous solution of a salt or of a salt mixture.

16. Half-cell according to claim 4, wherein the polymer electrolyte additionally comprises a mixture of an organic solvent and an aqueous solution of a salt.

17. Half-cell according to claim 7, wherein the salt is present in suspended form.

18. Half-cell according to claim 7, wherein the salt is selected from the group consisting of potassium chloride, sodium chloride, lithium chloride, potassium nitrate, potassium perchlorate, sodium formiate, lithium acetate, lithium sulfate, ammonium chloride, methyl-ammonium chloride, dimethyl-ammonium chloride, trimethyl-ammonium chloride and mixtures thereof.

* * * * *